United States Patent [19]

Griffith

[11] Patent Number: 4,998,532

[45] Date of Patent: Mar. 12, 1991

[54] PORTABLE ELECTRO-THERAPY SYSTEM

[75] Inventor: Neil Griffith, San Diego, Calif.

[73] Assignee: LTI Biomedical, Inc., San Diego, Calif.

[21] Appl. No.: 313,332

[22] Filed: Feb. 21, 1989

Related U.S. Application Data

[63] Continuation of Ser. No. 866,766, May 23, 1986, abandoned.

[51] Int. Cl.⁵ ............................................... A61N 1/00
[52] U.S. Cl. ................................................. 128/419 F
[58] Field of Search ..................... 128/422, 423, 419 F; 600/9, 10, 11, 12, 13

[56] References Cited

U.S. PATENT DOCUMENTS

| | | | |
|---|---|---|---|
| 4,266,532 | 5/1981 | Ryaby et al. | 128/419 F |
| 4,574,809 | 3/1986 | Talish et al. | 128/419 F |
| 4,587,957 | 5/1986 | Castel | 128/419 F |
| 4,619,264 | 10/1986 | Singh | 128/419 F |
| 4,620,543 | 11/1986 | Heppenstall et al. | 128/423 |
| 4,641,633 | 2/1987 | Delgado | 128/1.5 |
| 4,674,482 | 6/1987 | Waltoen et al. | 128/1.5 |

Primary Examiner—Francis Jaworski
Assistant Examiner—George Manuel
Attorney, Agent, or Firm—Brown, Martin, Haller & McClain

[57] ABSTRACT

A portable non-invasive apparatus for electro-therapeutic stimulation of tissue and bone healing readily worn or carried by a patient, capable of generating an energy-efficient signal coacting with a suitable transducer of the signal, thereby realizing portability and stimulating tissue and bone healing.

21 Claims, 5 Drawing Sheets

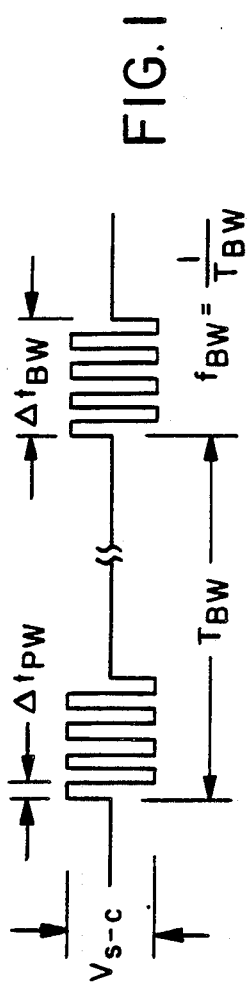

| COIL TYPE: | SIMPLE | OBLIQUE | SOLENOID | HELMHOLTZ |
|---|---|---|---|---|
| LIMB DIAMETER | $S$ | $S$ | $S$ | $S$ |
| $L(H)$ | $\dfrac{\pi S N^2 \times 10^{-7}}{2 \times 9.8}$ | $\dfrac{\pi\sqrt{3/2}\, SN^2 \times 10^{-7}}{2 \times 9.8}$ | $\dfrac{6\pi S N^2 \times 10^{-7}}{2\sqrt{2} \times 9.8}$ | $\dfrac{\pi S N^2 \times 1.1 \times 10^{-7}}{2\sqrt{2} \times 9.8}$ |
| $f_c \left(\dfrac{GAUSS}{AMP}\right)$ | $\dfrac{2\pi N}{5S}$ | $\dfrac{2\pi N}{5S\sqrt{3/2}}$ | $\dfrac{\pi N \sqrt{2}}{5S}$ | $\dfrac{\pi N \sqrt{2}}{5S\sqrt{3/2}}^{3/2}$ |
| $K_c$ | $1.02 \times 10^{-8} S^3$ | $1.87 \times 10^{-8} S^3$ | $0.861 \times 10^{-8} S^3$ | $5.33 \times 10^{-8} S^3$ |
| NORMALIZED | 1.18 | 2.17 | 1.0 | 6.19 |

PORTABLE ELECTRO-THERAPY SYSTEM

This is a continuation of application Ser. No. 06/866,766 filed May 23, 1986, now abandoned.

BACKGROUND OF THE DISCLOSURE

A variety of biochemical events, particularly changes in ion transport, protein synthesis and the like are involved in the repair of fractured bones. It has long been recognized that properly applied electro-therapy signals can stimulate bone growth in the vicinity of fresh fractures and non-union fractures, and apparently do so by initiating or stimulating the requisite biochemical changes. Extensive research has been conducted in both experimental animal studies and human clinical trials utilizing various specific waveform formats for such treatment, including invasively-coupled, direct-current devices; capacitively-coupled, symmetric and asymmetric waveforms, and electro-magnetically coupled asymmetric waveforms. Excellent technical reviews of this field are J. A. Spadaro's Bioelectric "Stimulations of Bone Formation: Methods, Models and Mechanisms", in the Journal of Bioelectricity, Volume 1 (1), p. 99, 1982; and the *Orthopedic Clinics of North America Symposium on Electrically Induced Osteogenesis*, W.B. Saunders Corp. 1984.

All currently used electro-therapy therapy techniques have one or more limitations. For example, invasive techniques have the potential of increasing the risk of infection, and unpredictable and potentially long-term side effects. Capacitively-coupled systems are limited by the fact that when operated at safe voltage levels, they require electrical connection between capacitive plates and the skin in the area surrounding the fracture site. Conductive jellies are typically employed and, by their nature, do not lend themselves to long-term installation. Electromagnetically, inductively-coupled techniques have required high power consumption waveform generation devices and bulky coil configurations that compromise the patient's ability to function normally outside of the clinical environment; Representative U.S. patents describing the above devices are 4,535,775, inventors Brighton and Pollack; 4,667,809, inventor Brighton; 4,467,808, inventors Brighton and Pollack; 4,266,532, inventor Ryaby; 3,952,751, inventor Yanger; 3,893,462, inventor Manning; and 3,890,953, inventors Kraus and Viehbach.

It generally takes bone fractures, particularly non-union fractures, many weeks or months to heal, and this is true even with the aid of electro-therapy where it has been tried as an adjunct treatment in an experimental setting. Because the presently utilized electro-therapy devices are, with a few exceptions, not truly portable, if the patient is to benefit from electro-therapy, he must have ready access to a source of electric power to effect treatment. Considering the time required for a bone to heal, this constraint is particularly annoying on a day to day basis, and requires that a patient constantly interrupt his daily routine for treatment, which may in turn cause failure of the patient to comply with the required protocol. Therefore, it is apparent that it is desirable to produce a device having the effective features of the devices currently in use but lacking their undesirable features, particularly their power wasting aspects. By creating a more power-efficient electro-therapy device it is possible to considerably reduce the size of the electro-therapy machines, hence permitting the construction of a completely portable device that allows the user to go about his daily routine without being tethered to a source of electric power.

A few inventors have appreciated the practical advantages of having a portable electro-therapy device. It is important to note that portability in the art is taken to mean a device readily carried by the patient without cumbersome support aids, and particularly connotes devices less than two pounds in weight, and no larger than a conventional pocket camera. U.S. Pat. No. 4,432,361 describes a portable device that has self monitoring features thereby allowing the patient to ascertain its operational status without having to have it checked by a physician, or another person skilled in the use of the device. This invention is an improvement over that described in U.S. Pat. No. 3,842,841 which does not have the desirable self-monitoring features. Another portable electrotherapy device is described in U.S. Pat. No. 4,574,809. It shows a device suitable for integration into an orthopedic cast with a signal generator removably mounted in the cast.

SUMMARY OF THE INVENTION

This patent describes a portable electro-therapy device having considerable advantages over prior devices. In an exemplary embodiment of the invention, the deficiencies of prior art systems are overcome in a system in which an effective treatment signal is produced in a low power consumption device, and then efficiently coupled to the treatment site by transducers that may be conformed to the external body line contours in the vicinity of the treatment site so that the entire system lends itself to portable, ambulatory use. Prior to the Applicant's invention, it was generally assumed that the body did not respond to short duration symmetric electromagnetic pulses, resulting in the development of bulky circuit devices for generating the long-duration pulses thought necessary for effective treatment. Applicant has discovered an hithertofore unrecognized feature of the biology of healing realized by electro-therapy, particularly bone healing, but the effectiveness of the device encompasses healing of damaged tissues generally. The "effective treatment signal" of this invention comprises symmetrically shaped pulses, especially those of a relatively short pulse width, and especially grouped into a burst of pulses followed by a quiet time, which are as efficacious as devices applying other electrical parameters. This realization has permitted the design of a device using several orders of magnitude less power than required by existing devices. This finding, coupled with conformal transducer designs for delivering the low power signal to the damaged tissue site, permits the development of a truly electro-therapy device.

A variety of transducers of specific designs can contribute to the overall energy efficiency of the subject device. However in an exemplary embodiment of the invention, the conformal assembly complex comprises a solenoidal coil of varying turns applied around a limb and connected to a power source to generate signals at the treatment site.

As applied to healing of bone fractures, the application of the invention described herein in no way affects or interferes with present treatment protocols. Thus, the physician is given a treatment option especially for those fractures, for example, non-union fractures, which, by experience and analysis, have been determined to be most likely to require surgery or other invasive procedures.

BRIEF DESCRIPTION OF THE DRAWINGS

FIG. 1 shows an effective electro-therapeutic signal.

FIG. 3 compares the energy efficiencies of various coil transducers.

Figure 2:
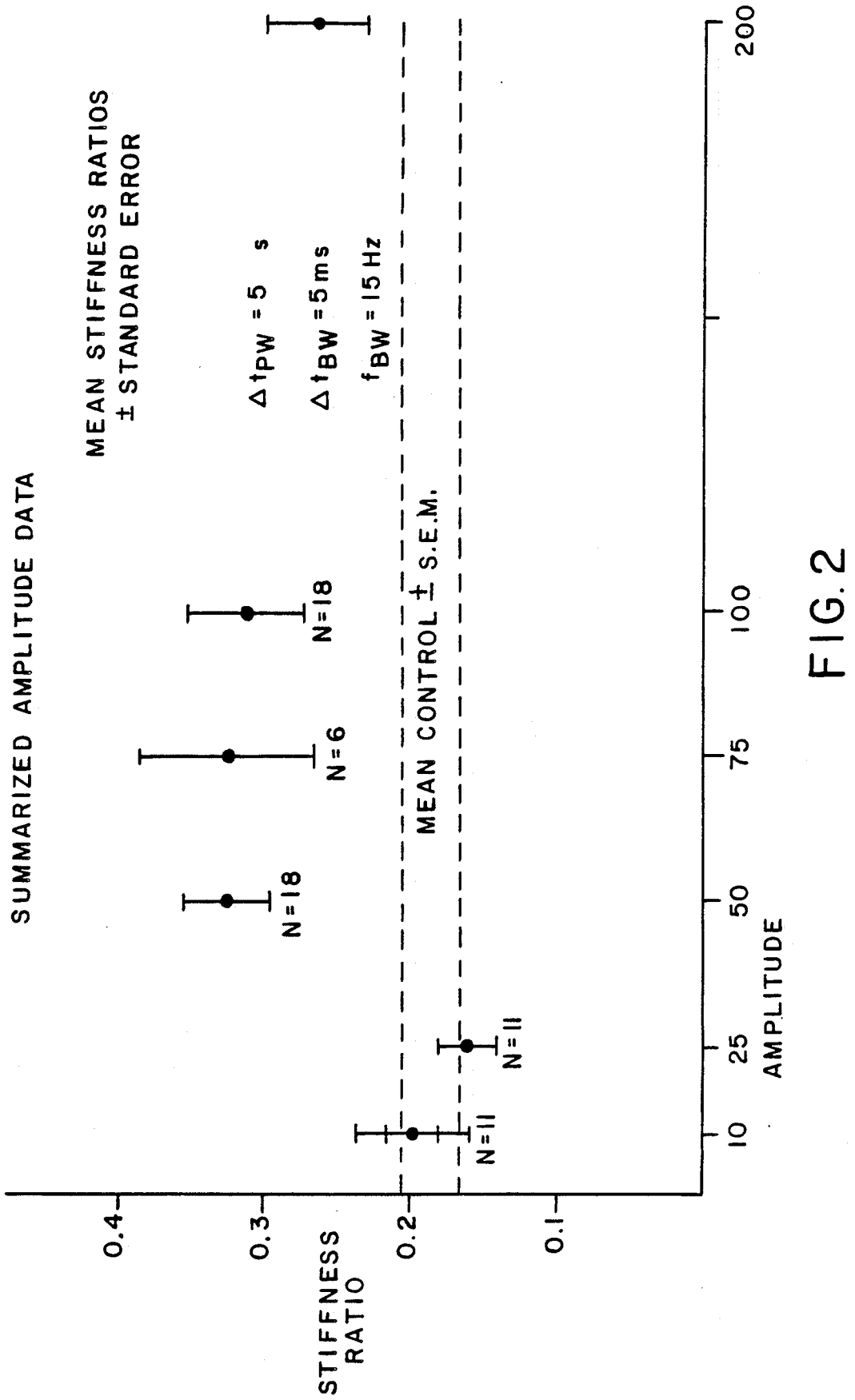
FIG. 2 relates the amplitude of an effective signal with the stiffness ratio when $\Delta t_{PW}=5\mu sec$, $\Delta t_{BW}=5msec$ and $f_{BW}=15Hz$.

Table I shows that an effective signal is realizable down as low as 0.5 $\mu$sec pulse width.

Table II shows stiffness ratios obtained at varying pulse widths-over the range 2–10 $\mu$sec.

Table III shows stiffness ratios obtained at varying amplitudes using 5 $\mu$sec pulse width.

Table IV shows the calculated ranges of useable hours of the electro-therapeutic device as a function of different batteries, coil number, and signal pulse width.

DETAILED DESCRIPTION OF THE INVENTION

It has been discovered that an electric signal of particularly unique parameters is able to stimulate healing of bone fractures, and damaged tissues, especially bone fractures that do not readily heal in the absence of treatment such as non-union fractures. However, the subject invention is equally effective in healing delayed unions and failed fusions.

The portable electro-therapy device described herein is based on experimental studies showing the therapeutic effectiveness of an electro-magnetic signal having a substantially symmetric waveform consisting of a train, having positive and negative amplitudes of pulses and of a particular range of burst widths, pulse widths, peak amplitudes and frequencies. A key feature of this signal is that it consumes nearly an order of magnitude less energy than current state-of-the-art devices using different signals. In part, this is because we have shown that the pulse width of an efficacious signal can be reduced down as low as 0.5 microseconds and still effect tissue healing. The electro-magnetic field, and associated power density established within the tissue is proportional to dB/dt, or the rate of change of the magnetic flux density, and thus is independent of pulse width for dB/dt = constant. Since the power required to generate a signal is a function of the pulse width squared, the power needed to establish an efficacious signal can be reduced by narrowing the pulse width. Hithertofore, this aspect of the electrobiology of tissue healing, particularly bone healing, has not been appreciated.

Biological studies were conducted on an animal model system wherein the efficaciousness of the pulsed signal was established. The most reliable animal model for these studies has proven to be the rabbit fibular system as described by C.T. Brighton et al. in the *Journal of Orthopedic Research*, Volume 3, No. 3, 1985. In this system rabbits underwent a mid-shaft transverse osteotomy of one fibula, after which a suitable transducer connected to a power supply was installed over the fracture. Both experimental and control animals were treated with the signal shown in FIG. 1 where $V_{s-c}$ is the search coil voltage; $\Delta t_{PW}$ is pulse width; $\Delta t_{BW}$ is burst width and $f_{BW}$ is burst frequency. We have found that a $\Delta t_{PW\ between}$ 2 and 10 microseconds is therapeutically effective, with 5 microseconds being particularly effective. Presently used devices generate $\Delta t_{PW}$ in the ranges of 20 to 300 microseconds for asymmetric signals.

While we experimentally have shown that a $\Delta t_{PW}$ of 2–10 $\Delta$sec is effective, it will be readily appreciated by those skilled in the art that a $\Delta t_{PW\ of}$ 0.5–20 microseconds is therapeutically acceptable. This is anticipated from simple theoretical considerations. For instance, activation of the cellular machinery involved in bone or tissue repair by electro-magnetic radiation requires delivery of a signal to the injured site having defined time constants for burst, width and burst frequency. In order to realize this, it is necessary for the signal to traverse healthy tissue to reach the injured site, and thus not be attenuated before doing so. This in turn suggests that the time constants associated with the magnetic, electric, chemical, and electro-diffusion effects caused by the signal exhibit particular time constants. It will be appreciated, referring to Table I (from "Electric Fields, Forces, and Flows in Biological Tissue," Al Grodzinsky, MIT, July 1985) that the magnetic "diffusion" equation assures that below 100 MHz that the magnetic field completely penetrates through to the injured site. For electric, "diffusion", penetration of the bone by the electric field remains high until 1 MHz. Further, the viscous flow of interstital fluids in the canaliculi can follow frequencies up to one MHz. In contrast, however, mechanical stress frequency responses attenuate after 500 Hz. Although the exact mechanism for promotion of healing is not known, it is presumed that electrical penetration is required. Using the conductivity of bone (one of the least conductive forms of tissue) a rise time or $t_{pw}$ of 0.5 is required for a maximum efficacious $f_B$ of 1 MHz.

Electro-therapy was continued for a period of 16 days during which time $V_{s-c}$, $\Delta t_{PW}$ and duty cycle were varied. Following treatment, both control and experimental animals were sacrificed and the fractured fibula excised. The fibula were mechanically tested for 3 point bending stiffness in a CGS Lawrence testing apparatus as described by Brighton, discussed supra, and the maximum resistance to bending measured for all the fibulae. The stiffness ratios of the fractured to intact fibulae of the electrically stimulated rabbits was determined and compared to those of the non-stimulated rabbits.

Briefly, within about 30 minutes after sacrificing the animals, a deformation rate of about 4 mm/min. was used and the stiffness ratio determined. The stiffness ratio derived by ascertaining the slope of the load-deformation curve, or stiffness, of fractured and intact fibula in the same animal. In this way variation in fibular strength for individual animals is controlled. The stiffness ratios of animals in the experimental group were compared to those of control animals at various pulse widths and amplitudes.

Tables II and III illustrate the effectiveness of this invention by examples of stiffness ratio measurements over a range of pulse width in microseconds at 100 mV (Table II) and amplitudes in millivolts. In both Tables, $f_B=15Hz$ and $t_{BW}=5msec$. In Table II, $V_{s-c}=74mV$ and $\Delta t_{PW}$ varies from 2–10 usec. In Table III, $\Delta t_{PW}=5msec$ and $V_{x-c}$ varies from 10–200 mV. Also in both Tables, the average value of the stiffness ratio is denoted by $<x>$ or x, the standard deviation of the test data by SD or $\sigma$ and the number of samples per test by N. The search coil had 67 turns and a diameter of 5.8 mm.

The data in the Tables are readily interpreted from the descriptions of the experiment and the definitions of stiffness ratio given above. Stiffness measures the resistance to deformation of an object (e.g., a bone) under a given load; a higher value means a more rigid object. As noted above, the stiffness ratio compares the stiffness of an animal's intact fibual with the stiffness of the fibual on the same animal which has been broken and subsequently healed under the experimental conditions. The higher the stiffness ratio, the more the broken bone has healed and approaches the stiffness of the intact bone; i.e., the better the healing process. It will be evident from the data in Tables II and III that bones healed under the electrotherapy stimulation of the apparatus of the present invention were more completely healed than the bones of the control animals which have not been subjected to the electrotherapy, as is evidenced by the statistically significant greater stiffness ratios of the treated animals than of the control (non-stimulated) animals.

While the signal shown above, is particularly electrotherapeutically effective, it is to be anticipated that other signals in addition to the simple positive and negative square wave will be efficacious. Thus it should be emphasized that key features of a suitable signal are that it be symmetric, have a narrow pulse width as described above, and, moreover, display a bursted format. Thus it is to be anticipated that rectangular waves, sine waves and other wave forms with these properties will be therapeutically effective.

The above discussion shows that it is possible to effect healing of bone fractures at hithertofore unsuspected low pulse width signals. This finding led us to construct a small portable battery driven device capable of producing an efficacious signal with suitable strength ranging from 3–9 mv/cm at a distance of 2 cm. However, before we could take advantage of our electrotherapy observations which opened the door to portability, it was desirable to combine the signal generator with a more energy efficient transducer means for delivering the signal to the tissue damaged site. A determination of the optimal transducer design necessarily requires a consideration of the power efficiencies of various transducers. Further, partly determinative of the type of transducer that is favored for a particular application in the case of a bone fracture is the nature of the bone fracture sought to be treated. Thus, for deep non-union fractures, particularly those that occur to the femur, a transducer capable of delivering energy through considerable soft tissue is desirable. In contrast, a transducer requiring less power to maintain the same field strength can be employed for bone fractures nearer the skin, e.g. tibi or clavicle.

A coil-type transducer is most preferred for treating deep bone fractures. Consider, for example, that the power needed to be applied to a coil-type transducer (i.e. Helmholtz paired coils, simple coil, simple coil oblique to the fracture or solenoid) is:

$$P = (1 - n_{REC})\left(\frac{L}{2}\right)\left(\frac{1}{f_c}\right)^2 (V_{s-c} \cdot 4 \times 10^6)^2 \Delta t_{PW} \Delta t_{BW} f_B \quad \text{Equation 1}$$

where $n_{REC}$ is the fractional energy recovery coefficient, L is the coil inductance, $f_c$ is coil sensitivity, $V_{s-c}$ is search coil voltage, and $\Delta t_{PW}$, $\Delta t_{BW}$ and $f_B$ are pulse width, burst width and frequency respectively. It is apparent, therefore, that a coil constant reflecting the power efficiencies of the various types of coil transducers can be represented as:

$$K_c = \frac{L}{f_c^2}$$

A comparison of $K_c$ for several coil type transducers is shown in FIG. 3 reveals that a solenoid coil type transducer is the most energy efficient. Indeed, the order of energy efficient coil transducers is solenoid > simple coil > oblique > Helmholtz.

Figure 4:
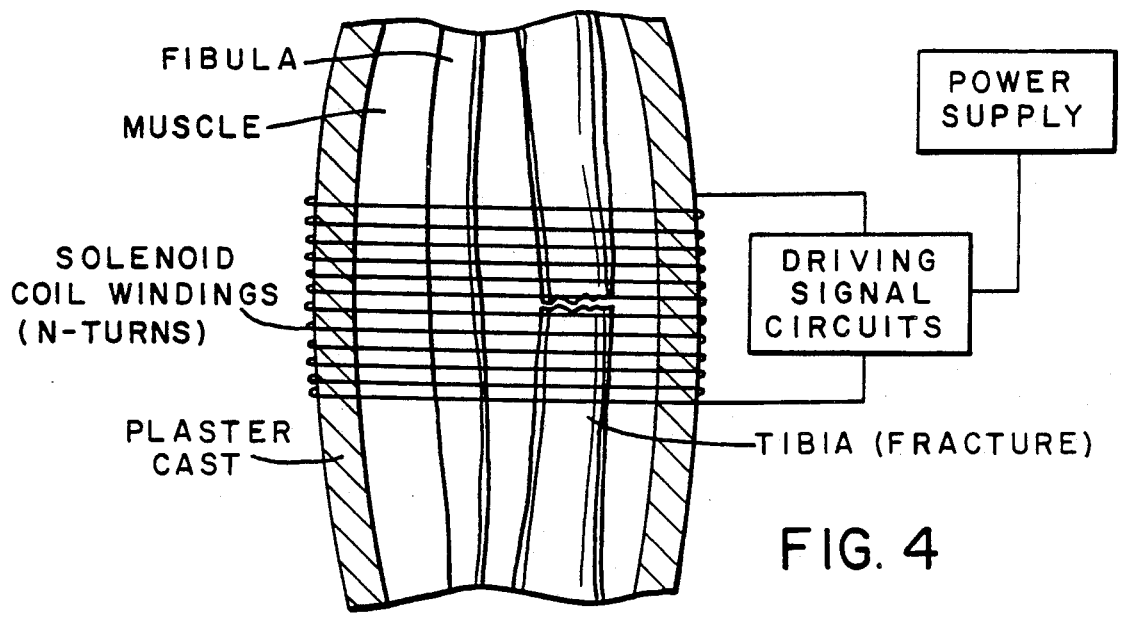
FIG. 4 displays a solenoid transducer positioned about a patient's leg with a fractured tibia.
Figure 5:
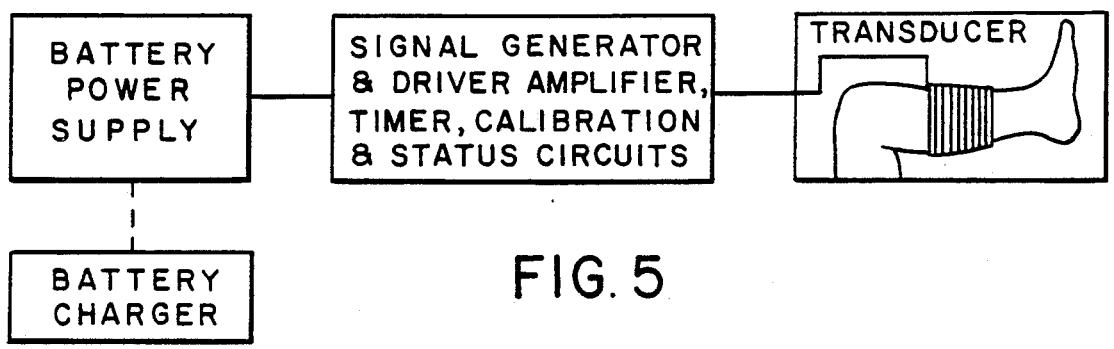
FIG. 5 reveals a block diagram of the subject invention.

It will be appreciated that when a conformal solenoid transducer for transmitting the signal shown in FIG. 1 is combined with a signal generating device, that the combination is capable of being integrated into a cast or associated therewith. An example is shown in FIG. 4. It will be further appreciated that while a conformal solenoid is preferred, that the other coil transducers may also be employed. Thus, a truly portable electrotherapy unit is readily constructed for treating shallow or deep fractures. FIG. 5 presents a typical block diagram for this unit.

Figure 9:
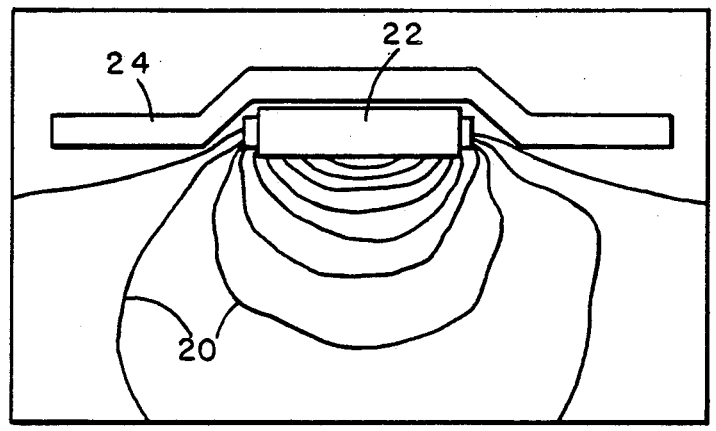
FIG. 9 depicts the lines of flux of the magnetic field established by a shielded dipole.
Figure 6:
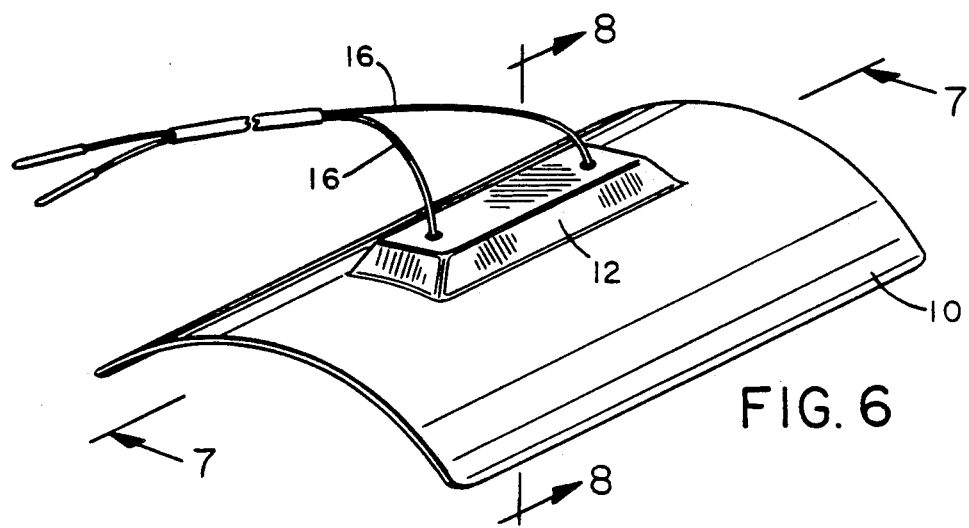
FIG. 6 depicts a perspective view of a conformal magnetic dipole transducer.
Figure 7:
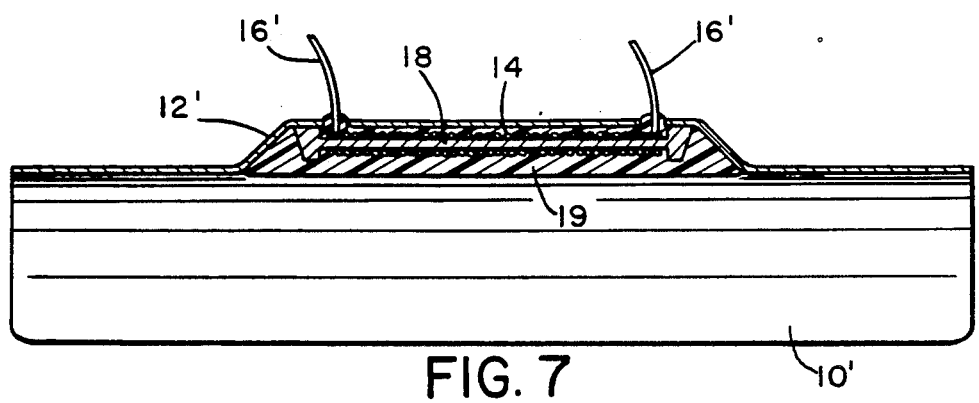
FIG. 7 is an enlarged sectional view taken on line 7—7 of FIG. 6.
Figure 8:
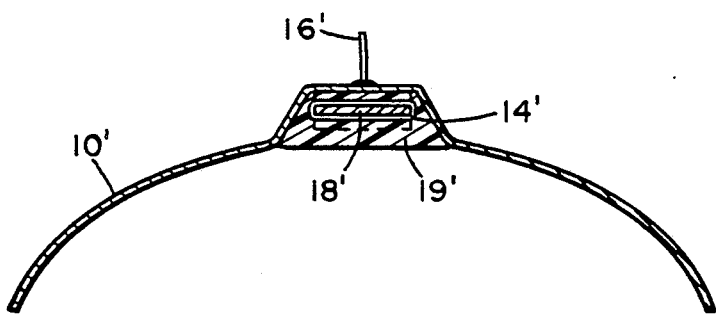
FIG. 8 is an enlarged sectional taken on line 8—8 of FIG. 6.
Figure 10:
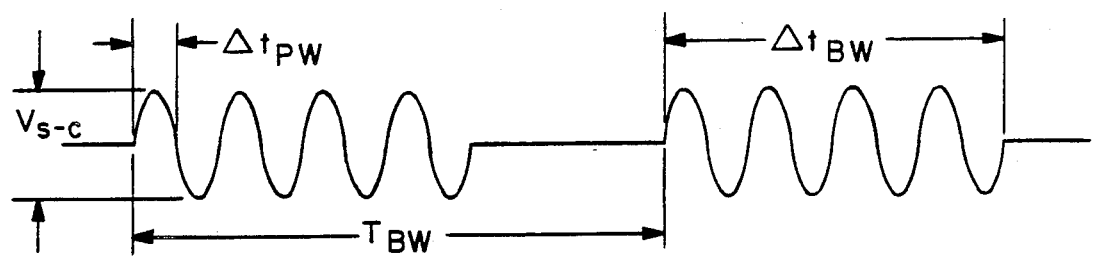
FIGS. 10 and 11 are equivalent to FIG. 1 and illustrate respectively a sinusoidal wave pulse train and triangular wave pulse train.
Figure 11:
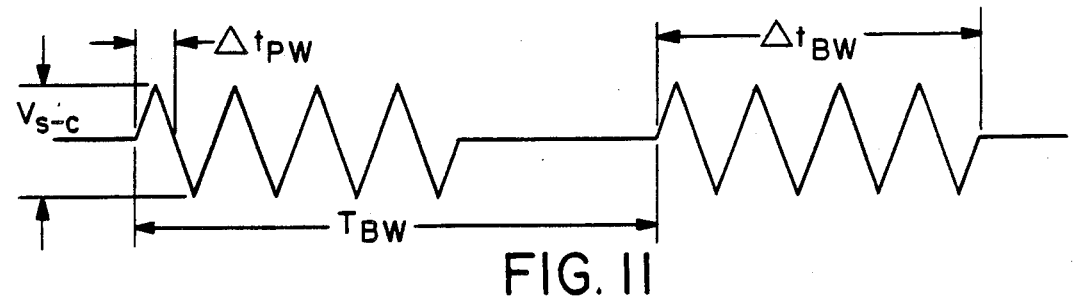

Another exemplary transducer is the conformal, magnetic dipole (CMD) which efficiently establishes shallow, focused fields on relatively superficial fractures, such as the tibia, ulna, radius, clavicle, or scaphoid. Whereas other transducers, simple coils, Helmholtz coils, etc., establish large, power-wasting fields external to the transducer, the CMD "captures" these extraneous fields and redirects them towards the fracture zone, effecting a 20–40% power savings while reducing exposure of the remaining body regions to extraneous fields. FIGS. 6–8 show an example of a conformal magnetic dipole transducer. In FIGS. 6–8 the transducer exhibits a metal shield 10, 10' having an uplifted region 12, 12' for housing the transducer coils 14, 14'. Current is supplied by the wires 16, 16' and flows through the coils 14, 14' wrapped about a suitable support element 18, 18'. The latter is held in place by glue, resin or the like 19. FIG. 9 shows the lines of flux 20 of the magnetic field emitted from the conformal magentic dipole 22 below the shield 24. It will be appreciated that by directing the magnetic field in a preferred direction that there is a considerable savings in energy.

It will be apparent that portability can be realized by integrating, or in some way associating, the transducer with the cast and having the power source and signal generator removed a short distance away. For example, the latter components might be attached to the user's waist belt and connected via leads to the transducer. Alternately, all the components may be attached to, or integrated into the cast. The former situation may be favored when a patient needs constant electrostimulation which may necessitate frequent replacement of batteries. On the other hand, for patients with minor fractures the duty cycle needed for maximum rate of healing may be considerably reduced, and there may be no need to change batteries over the required stimulation period. Here it might be desirable, for convenience to the patient and esthetic purposes, to integrate the entire unit in the cast.

It is anticipated that the power source used to generate the therapeutic signal will weigh less than 2 pounds and be about the size of a medium size hand-held pocket camera.

It will be appreciated that because of the energy efficiency of the electro-therapy device that the user will not have to replace the batteries for at least days, and perhaps not for months. Table IV shows the approximate number of useable hours of a device driven by particular batteries when the device has a solenoid transducer with a diameter of 12.7 cm, an l/d ratio of about 1, and a resistance of 0.63 ohm. Varying these parameters will, of course, effect the size of the batteries needed to achieve treatment Furthermore, it will be noted that the information in the table was derived using the equation:

$$I_B = I_{OH} + \left[ \frac{K_L V_{s-cp-p}^2 \Delta t_{PW}^2}{V_S N^2} (R_g + r/t\, N) - (\Delta t_{BW} \cdot f_{BW}) - \left( \frac{2}{V_S} \times 10^{-3} \right) \right] \quad \text{Equation 2}$$

where: $I_B$: Batt-Current
$I_O H$: Overhead Current
$K_c$: Coil Constant
$\Delta t_{PW}$: = pulse Width
N: Turns/Coil
$V_S$: Battery Voltage R: Driver Circuit, Output Resistance
r/t: Resistance/Turn
$\Delta t_B W$: Burst Width
$f_{BW}$: Burst Freq
and $V_{s-cp-p}=200$mv, $t_{PW}=5$msec, $t_{BW}=5$msec and $f_B=15$Hz.

An additional feature concerning the subject invention will be appreciated by referring to Equation 2 and Table III. It is apparent that "N", or the number of turns comprising the solenoid, is not invariant. By increasing or decreasing the number of turns it is possible to considerably alter the lifetime of the batteries used to drive the device. Thus for a particular application, N will be chosen to best effect the user's needs.

It will, of course, be understood that the foregoing examples and discussion exemplify only the general principles and materials applicable to the present invention. Numerous modifications are easily envisioned that may be employed without departing from the scope of the invention. For instance, as shown in FIG. 5, the device can be anticipated to be removably adapted to a cast and fitted with a battery charging unit so that the patient can effect recharging, should this be desirable, with reserve batter backs or during periods of non-treatment. Further, circuitry capable of tracking the length of time, or dose, of treatment, as well as visual or audible alarms to inform the patient of the same, are readily incorporated into the device. Moreover, the supporting experimental results described herein, and the particulars of the physical parameters of the electric signal used to achieve treatment, should not be viewed as being directly applicable to a human suffering from tissue or bone damage. It is the purpose of this invention to teach that a hithertofore unknown type of electric signal is efficacious for therapy, and when combined with a suitable transducer, yields a truly portable electro-therapeutic device. Thus, experimentation easily conducted by one skilled in the art can establish the details needed to effectively scale up the present invention for use in humans.

TABLE I

| PHYSICAL EFFECT | DEFINING EQUATION | $\tau$ TIME CONSTANT | $f_B = \frac{1}{T}$ EQUIVALENT BREAK FREQUENCY | EQUIV. $\Delta t_{PW}$ | PARAMETERS |
|---|---|---|---|---|---|
| MAGNETIC DIFFUSION | $\frac{\delta H}{\delta t} = \frac{1}{\mu\sigma}\nabla^2 H$ | $S^2\mu\sigma$ | $\frac{2}{(25 \times 10^{-4}) \times 4\pi \times 10^{-7}} \approx 100$ MHz | | $\mu$ = permeability $\sigma$ = conductivity H = field |
| ELECTRIC DIFFUSION | $\nabla \cdot \sigma E = \frac{\delta \rho}{\delta t}$ | $\frac{\epsilon}{\sigma}$ | $\frac{1}{10^{-9}, 10^6} \approx 1$ MHz $-$ 1 GHz | 0.5 $\mu s$ | $\epsilon$ = permitivity $\mu$ = permeability |
| VISCOUS DIFFUSION | $\frac{dV}{dt} = \frac{n}{\rho} \nabla^2 V$ | $\frac{\rho R^2}{n}$ | $\frac{10^{-3}}{10^3 (10^{-6})^2} \approx 1$ MHz | 5 $\mu S$ | n = viscosity $\rho$ = density R = channel radius (1 $\mu$m) |
| MECHANICAL | | $\frac{\delta^2}{mk}$ | $\frac{.5 \times 10^{+6} \times 10^{-15}}{10^3(10^{-6})^2} \approx 500$ Hz | | m = .modulus k = HYD Constant |

TABLE II

| | | STIFFNESS RATIOS PULSE WIDTH ($\mu$s) @ 100 mV | | | | | |
|---|---|---|---|---|---|---|---|
| EXPERIMENT | CONTROL | 2 | 3 | 4 | 5 | 7 | 10 |
| 9 May | $<X> = 1.20$ SD = 0.78 N = 6 | | | | | | $<X> = .366$ SD = .194 N = 9 |
| 11 June July | $<X> = .236$ SD = .147 N = 7 | | | | $<X> = .312$ SD = .175 N = 18 | | |

TABLE II-continued

STIFFNESS RATIOS
PULSE WIDTH (μs) @ 100 mV

| EXPERIMENT | CONTROL | 2 | 3 | 4 | 5 | 7 | 10 |
|---|---|---|---|---|---|---|---|
| 16 Oct.-Nov. | <X> = .244<br>SD = .114<br>N = 4 | | | | <X> = .302<br>SD = .166<br>N = 5 | | |
| 18 Nov.-Dec. | <X> .207<br>SD = .009<br>N = 2 | <X> =.225<br>SD = .097<br>N = 6 | | | <X> = .216<br>SD = .156<br>N = 6 | | |
| 19 Jan. | <X> = .156<br>SD = .029<br>N = 5 | <X> = .265<br>SD = .204<br>N = 9 | | <X> = .156<br>SD = .029<br>N = 5 | | | |
| 22 Feb. | <X> = .156<br>SD = .030<br>N = 6 | | | | | <X> = .301<br>SD = .043<br>N = 7 | |

TABLE III

STIFFNESS RATIO

| EXPERIMENT | CONTROL | 10 | 25 | 50 | 75 | 100 | 125 | 200 |
|---|---|---|---|---|---|---|---|---|
| 9 May | x = .120<br>σ = .078<br>N = 6 | | | | | | | x = .266<br>σ = .194<br>N = 16 |
| 10 June | x = .128<br>σ = .044<br>N = 6 | | | | | | | x = .142<br>σ = .086<br>N = 9 |
| 11 June-July | x = .236<br>σ = .147<br>N = 7 | | | | | x = .312<br>σ = .175<br>N = 18 | | |
| 12.5 July-August | x = .201<br>σ = .097<br>N = 3 | | | x = .464<br>σ = .074<br>N = 7 | | | | |
| 13.5 August | x = .224<br>σ =<br>N = 1 | | | x = .214<br>σ = .079<br>N = 5 | | | | |
| 14 September | x = .226<br>σ = .107<br>N = 5 | x = .189<br>σ = .116<br>N = 11 | x = .113<br>σ = .072<br>N = 3 | | | | | |
| 15 September-October | x = .167<br>σ = .076<br>N = 4 | | x = .177<br>σ = .066<br>N = 8 | x = .275<br>σ = .098<br>N = 6 | x = .327<br>σ = .148<br>N = 6 | | | |
| 15.5 October | x = .288<br>σ = .104<br>N = 2 | | | | | x = .272<br>σ = .201<br>N = 8 | | |
| 16 October-November | x = .244<br>σ = .114<br>N = 4 | | | | | x = .295<br>σ = .139<br>N = 7 | x = .302<br>σ = .166<br>N = 5 | x = .359<br>σ = .237<br>N = 8 |

TABLE IV

| Battery Type | $V_{Bmin}$ | N | $\mu S$ $t_{pw}$ | $I_{BA}$ mA | Cap mA-hrs | Dur Hrs | Wt g |
|---|---|---|---|---|---|---|---|
| 12⅜ AA NiCAD | 13.2 | 20 | 5 μS | 16.4 | 300 | 18.3 | 148 |
| 15⅜ AA NiCAD | 16.5 | 26 | 5 μS | 8.7 | 300 | 34.4 | 1858 |
| 3 × 9 V NiCAD | 23.1 | 37 | 5 μS | 3.7 | 100 | 27 | 138 |
| 2 × 9 V Alkaline | 12 | 19 | 5 μS | 21.6 | 450 | 21 | 92 |
| 3 ×9 V | 18 | 28 | 5 μS | 6.9 | 450 | 65 | 138 |
| P. P. Lithium (2) | 10 | 15 | 5 μS | 37.2 | 1300 | 35 | 68 |
| 6⅜ A Lithium | 15 | 23 | 5 μS | 11.4 | 916 | 80 | 81 |
| 2 "9 V" Zn AIR | 13 | 20 | 5 μS | 17.1 | 700 | 41 | 60 |
| 9⅜ Lithium | 22.5 | 35 | 7 | 7.1 | 916 | 129 | |
| 15⅜ AA NiCAD | 16.5 | 26 | 7 μS | 16.6 | 300 | 18.1 | |
| 3 "9 V" NiCAD | 23.1 | 37 | 7 μS | 6.65 | 100 | 15 | |
| 3 "9 V" Akaline | 18 | 28 | 7 μS | 13 | 450 | 35 | |
| 2 "9 V" Zn-AIR | 13 | 20 | 7 μS | 33 | 700 | 21 | |
| 6 9 V Akaline | 36 | 57 | 7 | 2.4 | 450 | 188 | |
| 2 9 V Akaline | 12 | 19 | 3 μS | 8.1 | 450 | 56 | |
| 3 9 V Akaline | 18 | 28 | 3 μS | 2.9 | 450 | 157 | |
| 6⅜ A Lithium | 15 | 23 | 3 μS | 4.5 | 916 | 204 | |
| 15⅜ AA NiCAD | 16.5 | 26 | 3 μS | 3.5 | 300 | 86 | |
| 6⅜ A Lithium | 15 | 23 | 10 | 44 | 916 | 21 | |
| 9⅜ A Lithium | 27.5 | 36 | 10 | 13.9 | 916 | 66 | |
| 3 PP Lithium | 15 | 23 | | 44 | 1300 | 30 | |

I claim:

1. A portable apparatus for electro-therapy of bone fractures comprising:
   a source of electric power connected to a means for converting said electric power into a series of substantially amplitude-symmetric voltage cycles, said voltage cycles comprising a train of bursted pulses having a pulse width of 0.5-20 microseconds, and a transducer means connected to said source of electric power for receiving said symmetric voltage cycles positioned so that an electromagnetic field at a fracture site is generated by applying said electric power to said transducer.

2. An apparatus as described in claim 1 wherein said source of electric power is a battery having a voltage of about 10-40 volts and a volume of about 2-6 cubic inches.

3. An apparatus as described in claim 2 wherein said voltage cycle comprises a symmetric electric signal having a frequency of about 5-25 Hz, and a burst width of about 1-10 milliseconds.

4. An apparatus as described in claim 3 further comprising a voltage cycle having a peak to peak amplitude of greater than 25 mV and less than 200 millivolts 5. An apparatus as described in claim 3 wherein said electric signal is sinusoidal.

6. An apparatus as described in claim 3 wherein said electric signal is a rectangular wave.

7. An apparatus as described in claim 3 wherein said wave form is triangular.

8. An apparatus as described in claim 1 wherein said source of electric power weighs less than 2 pounds.

9. An apparatus as described in claim 1 wherein said transducer means is a coil transducer selected from the group consisting of a conformal solenoid, oblique coil, and simple coil.

10. An apparatus as described in claim 1 wherein said transducer means is a conformal solenoid.

11. An apparatus as described in claim 1 wherein said transducer means is a conformal magnetic dipole.

12. An apparatus as described in claim 1 wherein said transducer means is formed in a cast so that said transducer means is closely proximal to said fracture site.

13. A portable apparatus for stimulating tissue healing comprising a battery supplying power connected to a means for converting said power to a series of substantially amplitude-symmetric voltage cycles, said voltage cycles comprising a train of bursted pulses having a pulse width of approximately 2-10 microseconds, and a peak-to-peak amplitude of approximately 50-150 millivolts, and a transducer means connected to received said voltage cycles for transducing said voltage cycles into an electromagnetic field at a treatment site to stimulate tissue healing at said treatment site.

14. An apparatus as described in claim 13 wherein said source of battery power is 10-40 volts and has a volume of about 2-6 cubic centimeters.

15. A portable apparatus for stimulating tissue healing comprising a battery supplying power connected to a means for converting said power to a series of substantially amplitude-symmetric voltage cycles, said voltage cycles comprising a train of bursted pulses having a pulse width of approximately 2-10 microseconds, and a transducer means connected to receive said voltage cycles for transducing said voltage cycles into an electromagnetic field at a treatment site to stimulate tissue healing at said treatment site.

16. An apparatus as described in claim 15 wherein said source of electric power is a battery having a voltage of about 10-40 volts and a volume of about 2-6 cubic centimeters.

17. An apparatus as described in claim 15 wherein said transducer means is a coil transducer selected from the group consisting of a conformal solenoid, oblique coil, and simple coil.

18. An apparatus as described in claim 15 wherein said transducer means is a conformal solenoid.

19. An apparatus as described in claim 15 wherein said transducer means is a conformal magnetic dipole.

20. An apparatus as described in claim 15 wherein said transducer means is formed in said cast so that said transducer means is closely proximal to said treatment site.

21. A portable apparatus for stimulating tissue healing comprising battery power connected to a means for converting said battery power to a series of substantially amplitude symmetric voltage cycles, said voltage cycles comprising a train of bursted pulses, and a transducer means connected to receive said voltage cycles for transducing said voltage cycles into an electromagnetic field at a treatment site to stimulate tissue healing at said treatment site.

* * * * *

UNITED STATES PATENT AND TRADEMARK OFFICE
CERTIFICATE OF CORRECTION

PATENT NO. : 4,998,532

DATED : March 12, 1991

INVENTOR(S) : Neil Griffith et al.

It is certified that error appears in the above-identified patent and that said Letters Patent is hereby corrected as shown below:

On the title page item [75] add the following inventors;

--Neil Griffith; Carl T. Brighton; Solomon R. Pollack and David Pienkowski--

Signed and Sealed this

First Day of December, 1992

*Attest:*

DOUGLAS B. COMER

*Attesting Officer*  *Acting Commissioner of Patents and Trademarks*

UNITED STATES PATENT AND TRADEMARK OFFICE
CERTIFICATE OF CORRECTION

PATENT NO. : 4,998,532

DATED : March 12, 1991

INVENTOR(S) : Neil Griffith

It is certified that error appears in the above-identified patent and that said Letters Patent is hereby corrected as shown below:

Title Page:

Column 1, Line 63 "866,766" should read --866,877--

Signed and Sealed this

Thirteenth Day of April, 1993

Attest:

STEPHEN G. KUNIN

*Attesting Officer*      Acting Commissioner of Patents and Trademarks